United States Patent [19]

Weigel

[11] Patent Number: 5,395,357
[45] Date of Patent: Mar. 7, 1995

[54] SPLATTER-FREE EAR IRRIGATION DEVICE

[76] Inventor: Perry L. Weigel, 218-2nd Ave., Box 126, Van Meter, Iowa 50261

[21] Appl. No.: 106,593

[22] Filed: Aug. 16, 1993

[51] Int. Cl.$^6$ .......................... A61F 5/44; A61F 11/00
[52] U.S. Cl. ...................................... 604/346; 128/866
[58] Field of Search ................ 604/346; 128/846, 849, 128/851, 852, 853, 854, 857, 864, 866; 2/423

[56] References Cited

U.S. PATENT DOCUMENTS

| | | | |
|---|---|---|---|
| 989,839 | 4/1911 | Fowler | 604/346 |
| 1,500,927 | 7/1924 | Davies et al. | 604/346 |
| 3,210,816 | 10/1965 | Clemons | 128/852 |
| 3,841,325 | 10/1974 | Pickard | 604/346 X |
| 3,972,332 | 8/1976 | Wakim | 128/853 |
| 4,036,235 | 7/1977 | Hathaway | 604/346 |
| 4,201,212 | 5/1980 | Bradley | 604/346 |
| 4,553,538 | 11/1985 | Rafelson | 128/852 |
| 4,834,068 | 5/1989 | Gottesman | 128/846 X |
| 4,926,882 | 5/1990 | Lawrence | 128/853 X |
| 4,949,734 | 8/1990 | Bernstein | 128/897 |

FOREIGN PATENT DOCUMENTS 670158 10/1965 Belgium ............... 128/866

*Primary Examiner*—Randall L. Green
*Assistant Examiner*—Mary Beth O. Jones
*Attorney, Agent, or Firm*—Brian J. Laurenzo; Kent A. Herink; Brett J. Trout

[57] ABSTRACT

A substantially closed apparatus for deflecting and retaining waste fluids issuing from the ear canal of a patient being irrigated by a caregiver. The device is preferably transparent thereby allowing the caregiver to accurately manipulate the irrigator within the ear canal and to monitor the waste retainer to determine when the container must be emptied. The substantially closed configuration of the device prevents waste fluids issuing from the ear canal from contacting and contaminating the caregiver which could result in the transfer of infection and disease.

11 Claims, 2 Drawing Sheets

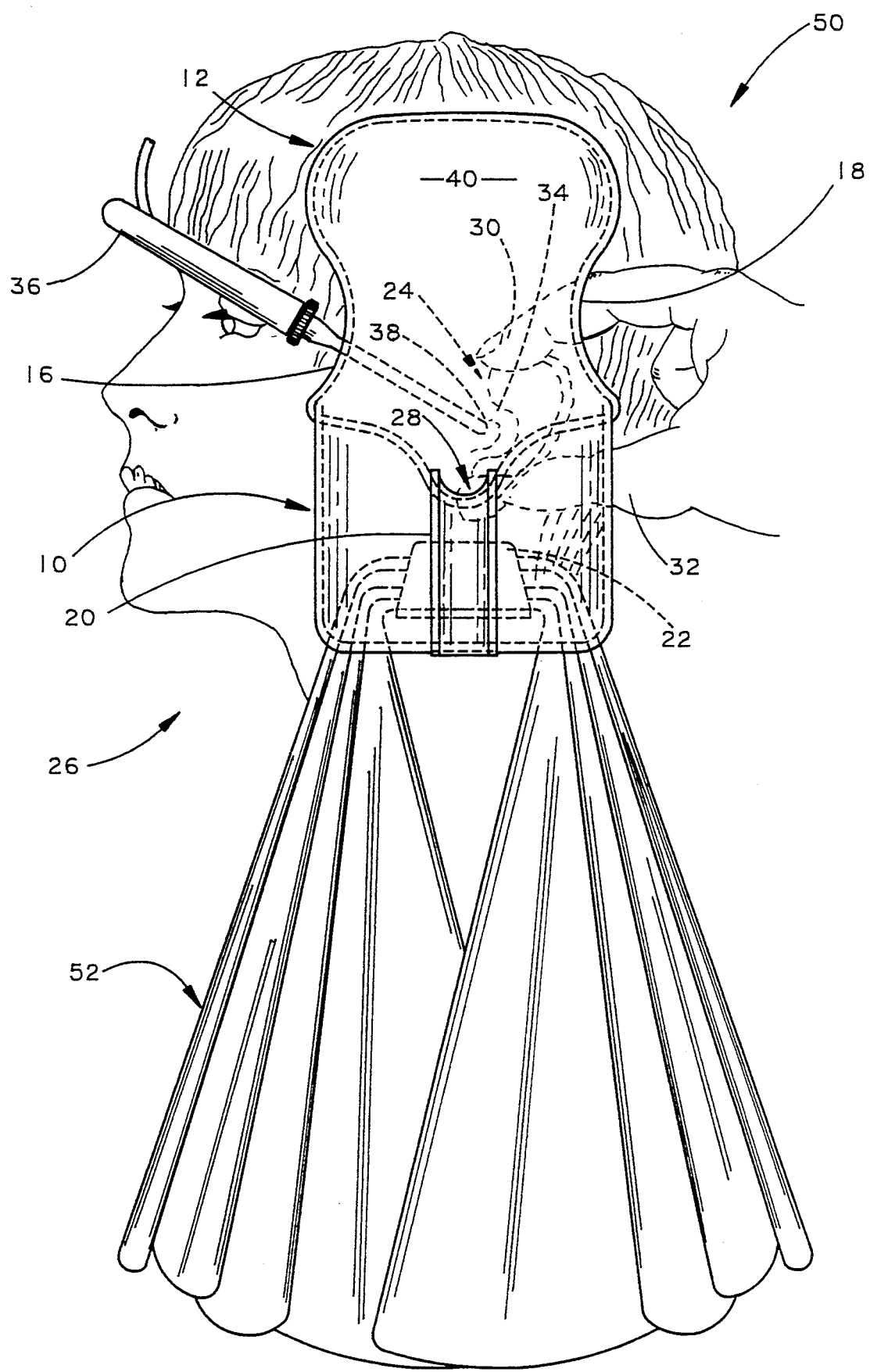

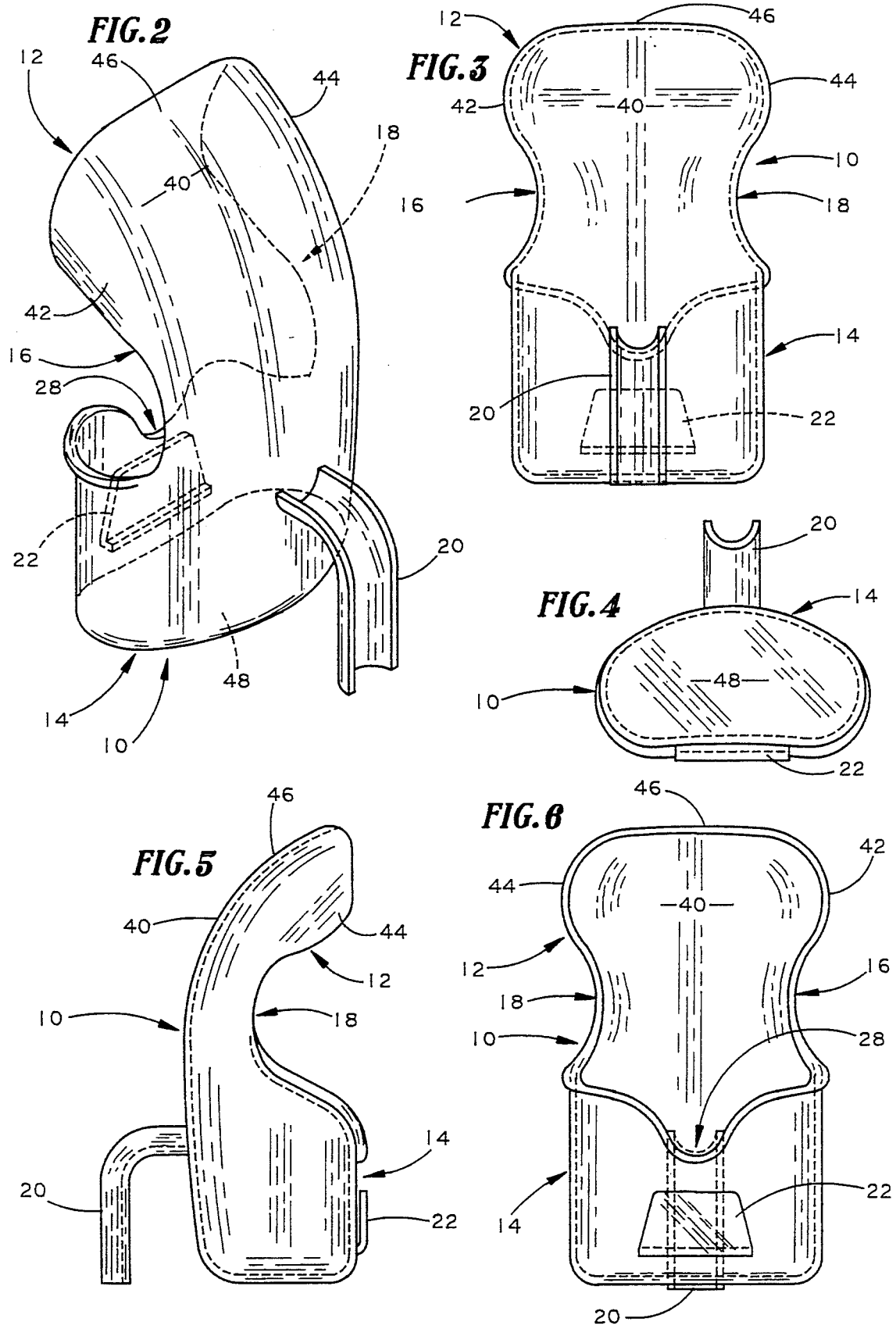

SPLATTER-FREE EAR IRRIGATION DEVICE

BACKGROUND OF THE INVENTION

The invention relates to an ear irrigation device and, more particularly, to a device for deflecting and receiving fluid and waste issuing from a patient's ear as the ear is being irrigated by a caregiver.

Ear irrigation for the removal of wax and other waste from the ear is well-known and many devices are available to receive such waste issuing from a patient's ear during irrigation. Some devices, such as U.S. Pat. No. 989,839 are of a single piece construction which totally encloses the patient's ear. Although such a device protects a caregiver from the fluid and waste during the irrigation procedure, such a device is of limited usefulness in that the portion of the device extending into the patient's ear has a fixed orientation. This fixed orientation is a result of the seal which must be in place, between the waste deflector and the portion of the device entering the patient's ear, to protect the caregiver from contact with the waste. Conversely, devices such as that shown in U.S. Pat. No. 4,201,212 have been developed which allow liberal access to a patient's ear, but expose the caregiver to possible dangerous contaminants from the ear during the irrigation process.

The caregiver's mucosa, especially the caregiver's eye mucosa is especially susceptible to contamination due to contact with waste issuing from a patient's ear. During irrigation of a patient's auditory canal, the caregiver must often place their eyes very close to the auditory canal to accurately manipulate the irrigator within the patient's ear. Given the obvious unpleasantness, as well as possible deleterious consequences of caregiver mucosa contact with bodily waste and fluids, such as possible infection with HIV or hepatitis, it is desirable to provide an apparatus for capturing fluid and waste issuing from a patient's ear during irrigation. Ideally, such a device would not hinder the irrigation procedure, but would allow liberal manipulation of the irrigator while protecting the caregiver from exposure to the waste products.

Even a combination of the two aforementioned prior art devices would not produce an effective apparatus. Because both apparatuses disclose inserting an irrigation device normal to the plane of the ear, the aperture allowing the irrigator access to the ear must be of a sufficient area to allow manipulation of the irrigator. An opening of sufficient size to allow manipulation of the irrigator, however, would allow sufficient room for fluid and waste to escape in the direction of the caregiver leading to the undesirable contact of the waste and fluid with the caregiver.

The difficulties of the prior art discussed hereinabove are substantially eliminated by the present invention.

SUMMARY OF THE INVENTION

Accordingly, it is an object of the present invention to provide an ear irrigating device which prevents waste issuing from a patient's ear from contacting a caregiver.

It is another object of the present invention to provide an ear irrigating device which deflects and retains waste issuing from a patient's ear during irrigation.

Yet another object of the present invention is to provide an ear irrigating device which allows liberal manipulation of an ear irrigator within a patient's ear during irrigation of the ear.

Still another object of the present invention is to provide an ear irrigating device which provides a caregiver with a shielded vantage of a patient's ear to thereby allow more precise irrigation of the ear.

By the present invention, it is proposed to overcome the difficulties encountered heretofore. To this end, a spray shield apparatus is provided for shielding a caregiver from exposure to waste issuing from an auditory canal of a patient during irrigation of the auditory canal. The apparatus is provided with means for retaining the waste, as well as means for deflecting the waste into the retaining means. The deflecting means is provided with a primary aperture of a sufficient size to allow insertion of an instrument therethrough. Means are also provided on the deflecting means for allowing the caregiver to visually monitor the ear through the deflecting means wherein the visual monitoring means also acts to deflect waste away from the caregiver.

In the preferred embodiment of the present invention, the apparatus is constructed of a clear plastic with the deflecting means comprising a body and three flanges substantially surrounding the ear. Depending from the deflection means is a retainer which is also preferably constructed of a clear plastic to allow the caregiver to monitor the amount of waste being collected. The primary aperture is provided in the side of the apparatus, above the waste retainer and below one of the side flanges of the deflecting means. A second aperture may also be provided on the opposite side of the apparatus to allow secondary access to the auditory canal during irrigation.

BRIEF DESCRIPTION OF THE DRAWINGS

In the drawings:

FIG. 1 is a side elevational view showing the ear irrigating device of the present invention with an ear irrigator positioned in one aperture and a caregiver's fingers positioned within a second aperture to manipulate the patient's ear during irrigation.

FIG. 2 is a perspective view of the present invention.

FIG. 3 is a front elevational view of the present invention.

FIG. 4 is a bottom view of the present invention.

FIG. 5 is a side elevational view of the present invention.

FIG. 6 is a rear elevational view of the present invention.

DETAILED DESCRIPTION OF THE PRESENT INVENTION

An ear irrigation apparatus 10 is shown having a cover 12 and a waste retainer 14. The apparatus 10 is constructed so as to substantially conform to a head 50 of a patient 26 and to substantially conform to an ear 24 of the patient 26 during the irrigation process. The apparatus 10 is preferably constructed of a transparent material to thereby allow a caregiver to accurately observe the irrigation process. As fluid and waste issue from an auditory canal 38, the fluid and waste either fall directly into the waste retainer 14 or deflect off the cover 12 into the waste retainer 14. The provisions of apertures 16 and 18 on the sides of the apparatus 10 allow liberal access to the ear 24 while substantially eliminating the possibility of caregiver contact with the fluid and waste during the irrigation process.

In the figures, there is shown the ear irrigation apparatus 10 having the cover 12, the waste retainer 14, and the apertures 16 and 18. In the preferred embodiment of the present invention, a curved handle 20 is secured to the front of the apparatus 10 while a towel clip 22 is secured to the rear of the apparatus 10.

In use, the apparatus 10 is placed over the patient's ear 24 and held with the handle 20 by the caregiver tending to the ear 24 (FIG. 1). The apparatus 10 is preferably constructed of a transparent material, such as polymethyl methacrylate, to allow the caregiver proper vantage when administering care to the ear 24.

The waste retainer 14 is provided with a recess 28 along the rear of the retainer 14 which allows the apparatus 10 to be properly positioned under the ear 24 of the patient (FIGS. 1 and 6). To use the apparatus 10, a caregiver grasps the handle 20 of the apparatus 10 and positions the recess 28 of the retainer 14 under the ear 24 of the patient to brace the apparatus 10 against accidental lateral or vertical displacement during irrigation of the ear 24 (FIG. 1).

Once the apparatus 10 has been properly positioned, the caregiver may insert a finger 30 and a thumb 32 through one of the apertures 18 to manipulate the pinna 34 of the ear into a proper orientation (FIG. 1). The apparatus 10 is preferably constructed with a second aperture 16, as shown in FIG. 1, to allow the insertion of the irrigator 36 into the auditory canal 38. Alternatively, the apparatus 10 may be held in place by a second caregiver so that either two instruments or an instrument and a hand 40 may be inserted through the apertures simultaneously. The ear 24 may thereby be manipulated as the ear 26 is being irrigated. The apertures 16 and 18 are preferably large enough to allow liberal manipulation of the irrigator 36 and the fingers 30 and 32 within the apparatus 10. As shown in FIG. 5, the apertures 16 and 18 are arcuate and bordered on three sides by the apparatus 10. When the apparatus is placed against the head 50 of the patient 26, the apertures 16 and 18 are fully surrounded, thereby substantially preventing any waste from escaping the apparatus 10, while still allowing liberal manipulation of the irrigator 36 within the apparatus 10 (FIG. 1).

The placement of the apertures 16 and 18 on the sides of the apparatus 10 has several advantages. One particular advantage is that, unlike many prior art devices, no fluid or waste issues directly toward the apertures 16 and 18, thereby significantly reducing the amount of waste and fluid escaping into the external environment through the apertures 16 and 18. Additionally, the side placement is advantageous in that any waste or fluid which may happen to escape through the apertures 16 and 18 will be moving laterally in relationship to the caregiver and therefore have very little chance of contacting the caregiver during the irrigation process. Still another advantage of the side placement of the apertures 16 and 18 is that the caregiver is able to witness the irrigation process much more clearly than if the irrigator 36 was being manipulated within the auditory canal 38 along a line parallel to the auditory canal 38 and thereby blocking the most advantageous view of the irrigation process.

As the irrigator 36 begins to flush the ear 24 with fluid, the fluid begins to issue from the ear 24 as waste which includes the fluid as well as wax and other material flushed from the ear 24 (FIG. 1). To prevent such waste from contacting the caregiver, the cover 12 consists of a body 40, a pair of side flanges 42 and 44, and a top flange 46 which coact to deflect the issuing waste downward toward the waste retainer 14 (FIGS. 2 and 5). The transparent construction of the body 40 and the cover 12 allows the caregiver to accurately view and manipulate the irrigator 36 within the ear 24 of the patient 26, even when waste is issuing directly toward the caregiver (FIGS. 1 and 3).

As the waste issues from the ear 24, the waste contacts the cover 12 (FIG. 1). The cover 12 is preferably constructed at a slight angle so that waste contacting the cover 12 is directed downward into the waste retainer 14 (FIG. 5). Waste contacting the cover 12 is either deflected directly into the waste retainer 14 or runs along the inner surface of the cover 12 down into the waste retainer 14.

As shown in FIG. 4, the waste retainer 14 has a bottom 48 which is preferably of a substantially kidney shape to accommodate the curvature of the cover 12 and head 50 of the patient 26 (FIGS. 1 and 4). It should be noted, however, that the bottom 48 of the waste retainer 14 may be constructed of any configuration which retains the waste and accommodates the cover 12 to prevent waste from passing around the cover 12 or retainer 14. The transparent construction of the entire apparatus 10 allows the caregiver to determine when the waste retainer 14 is full and must be emptied before continuing irrigation of the ear 24. In the preferred embodiment of the present invention, the apparatus 10 is sterilized before irrigation so that the waste issuing from the ear 24 and being deposited in the waste retainer 14 may be examined before being discarded.

The handle 20 is preferably connected to the apparatus 10 at a point substantially where the cover 12 meets the waste retainer 14, but may, of course, be mounted in any orientation which is easiest for the caregiver to handle during manipulation of the ear 24. Additionally, in the preferred embodiment of the present invention, the towel clip 22 is provided on the back side of the waste retainer 14 so that a towel 52 may be attached to the apparatus 10 to be hung down around a shoulder of the patient 26. The towel 52 absorbs waste escaping either between the waste retainer 14 and the head 50 of the patient or from either aperture 16 and 18. The towel 52 acts to absorb any excess waste before the waste rolls down the neck of the patient 26 to contact either the caregiver or the clothes of the patient 26.

Although the invention has been described with respect to a preferred embodiment thereof, it is to be also understood that it is not to be so limited since changes and modifications can be made therein which are within the full intended scope of this invention as defined by the appended claims. For example, it is anticipated that only one or several apertures may be provided in the apparatus and that the apertures may be provided in the flanges 42 and 44 so that the apertures are fully surrounded and are no longer merely surrounded by the apparatus 10 on only three sides.

I claim:

1. A spray shield apparatus for shielding a caregiver from exposure to waste issuing from an auditory canal of a patient during irrigation of the auditory canal, the spray shield apparatus comprising:
   (a) means for retaining said waste; and
   (b) a shield member operably connected to said retaining means, said shield member comprising a deflecting face to be positioned oppositely from the ear and two opposing sides integral with said deflecting face, at least one of said sides including a contour, said contour of a construction which allows insertion of an instrument therethrough;

(c) said deflecting face being free of apertures and of a construction which allows the caregiver to visually monitor the ear through said deflecting face while deflecting waste away from the caregiver and thereby protecting the caregiver from contact with the waste.

2. The apparatus of claim 1, wherein said shield member contacts the patient at at least one point above the ear to substantially deflect the waste from passing over said shield member and into contact with the caregiver.

3. The apparatus of claim 1, wherein a first side of said two opposite sides includes a first said contour and a second side of said two opposite sides includes a second said contour, said first and second contours both of a construction which allows insertion of an instrument to tend the ear, said second contour providing secondary access to the ear.

4. The apparatus of claim 1, wherein said shield member further comprises a top portion, said top portion and said two opposing sides having flanges which extend from said top portion and said two opposing sides of said shield member to contact the patient thereby substantially preventing the waste from passing over said top flange and around said side flanges into contact with the caregiver.

5. The apparatus of claim 3, wherein said first and second contours are located substantially laterally of said deflecting face and substantially above said retaining means.

6. The apparatus of claim 1, wherein said instrument is an auditory canal irrigator.

7. The apparatus of claim 1, wherein the apparatus is constructed of a transparent material.

8. The apparatus of claim 1, wherein said waste retaining means is provided with a recess which substantially conforms to the ear to position the apparatus more accurately during use.

9. The apparatus of claim 1, further comprising a handle connected to the apparatus to allow the apparatus to be held in place as the ear is being irrigated.

10. The apparatus of claim 1, further comprising a towel clip connected to the apparatus to allow a towel to depend from the apparatus as the ear is being irrigated so that waste escaping through the apparatus is prevented from contacting the patient.

11. The apparatus of claim 1, said contour being of a construction which allows said instrument to contact the auditory canal at a plurality of angles to more efficiently tend the ear.

* * * * *